US 6,593,574 B2

(12) United States Patent
Thomas et al.

(10) Patent No.: US 6,593,574 B2
(45) Date of Patent: Jul. 15, 2003

(54) HAND-HELD SOUND SOURCE GUN FOR INFRARED IMAGING OF SUB-SURFACE DEFECTS IN MATERIALS

(75) Inventors: Robert L. Thomas, Huntington Woods, MI (US); Lawrence D. Favro, Huntington Woods, MI (US); Xiaoyan Han, Plymouth, MI (US)

(73) Assignee: Wayne State University, Detroit, MI (US)

( * ) Notice: Subject to any disclaimer, the term of this patent is extended or adjusted under 35 U.S.C. 154(b) by 196 days.

(21) Appl. No.: 09/802,281

(22) Filed: Mar. 8, 2001

(65) Prior Publication Data

US 2002/0121602 A1 Sep. 5, 2002

Related U.S. Application Data

(63) Continuation-in-part of application No. 09/397,585, filed on Sep. 16, 1999, now Pat. No. 6,236,049.

(51) Int. Cl.⁷ .............................................. G01N 29/22
(52) U.S. Cl. .................... 250/341.6; 250/334
(58) Field of Search ............................. 250/341.6, 334, 250/338.1, 338.3, 332, 341, 330, 347; 73/620; 356/381, 237; 348/571

(56) References Cited

U.S. PATENT DOCUMENTS

| 3,934,452 A | 1/1976 | Prevorsek et al. |
| 4,229,658 A | * 10/1980 | Gonser .................... 250/504 R |
| 4,232,554 A | 11/1980 | Aleck |
| 4,378,701 A | 4/1983 | Mountain et al. |
| 4,463,608 A | 8/1984 | Takeuchi et al. |
| 4,541,059 A | 9/1985 | Toshihiko |
| 4,607,341 A | 8/1986 | Monchalin |

(List continued on next page.)

OTHER PUBLICATIONS

Database WPI, Section El, Week 199328, Derwent Publications Ltd., London, GB: XP–002230464 & SU 1 748 047 A (Orbinsk Tekhnologiya Sci Prodn Assoc), Jul. 15, 1992, abstract.

Database WPI, Section El, Week 199107, Derwent Publications Ltd., London, GB: XP–002230466 & SU 1 200 675 A (Murata Mfg Co Ltd), Jul. 7, 1990, abstract.

Database WPI, Section El, Week 198204, Derwent Publications Ltd., London, GB: XP–002230467 & SU 818 698 A (Mat Non–Dest Test), Apr. 10, 1981, abstract.

Database WPI, Section El, Week 198041, Derwent Publications Ltd., London, GB: XP–002230465 & SU 717 646 A (Lengd Shipbuilding), Feb. 25, 1980, abstract.

(List continued on next page.)

*Primary Examiner*—Constantine Hannaher
*Assistant Examiner*—Otilia Gabor
(74) *Attorney, Agent, or Firm*—John A. Miller; Warn, Burgess & Hoffmann, P.C.

(57) ABSTRACT

A system for the thermal imaging of sonically or ultrasonically excited subsurface defects in a structure. The system includes a hand-held sound source, a thermal imaging camera and a control unit. The sound source emits pulses of sound energy into the structure, and the camera generates images of defects in the structure that are heated by the sound energy. The control unit controls the operation of the sound source on the camera for timing purposes. The sound source includes a transducer that is positioned against the structure at a desirable location. The source further includes a pair of legs that are also positioned against the structure to define a plane in combination with the transducer. The length of each leg is adjustable relative to the length of the transducer so that the gun can be used against irregular surfaces. The legs include a rubber tip to further prevent the transducer from slipping on the structure. In an alternate embodiment, the gun includes three transducers that define a plane and act to stabilize the gun against movement.

33 Claims, 7 Drawing Sheets

U.S. PATENT DOCUMENTS

| | | | |
|---|---|---|---|
| 4,625,557 A | | 12/1986 | Rutherford |
| 4,710,030 A | | 12/1987 | Tauc et al. |
| 4,782,990 A | | 11/1988 | Patrikios et al. |
| 4,828,400 A | | 5/1989 | Boyce |
| 4,878,116 A | | 10/1989 | Thomas et al. |
| 4,950,897 A | | 8/1990 | Mandelis et al. |
| 4,950,990 A | | 8/1990 | Moulder et al. |
| 4,961,346 A | * | 10/1990 | Salvado et al. ............... 73/644 |
| 5,137,200 A | | 8/1992 | Edwards et al. |
| 5,201,582 A | | 4/1993 | Lesniak |
| 5,201,841 A | | 4/1993 | Lebeau et al. |
| 5,287,183 A | | 2/1994 | Thomas et al. |
| 5,376,793 A | | 12/1994 | Lesniak |
| 5,417,494 A | | 5/1995 | Kempa et al. |
| 5,476,010 A | | 12/1995 | Fleming et al. |
| 5,495,763 A | | 3/1996 | Rhodes et al. |
| 5,567,881 A | * | 10/1996 | Myers ........................ 73/629 |
| 5,748,318 A | | 5/1998 | Maris et al. |
| 5,837,896 A | | 11/1998 | Rhodes et al. |
| 6,382,967 B1 | * | 5/2002 | Rohner et al. ............... 433/29 |
| 2002/0013954 A1 | * | 1/2002 | Yang et al. ................. 800/14 |
| 2002/0036617 A1 | * | 3/2002 | Pryor ........................ 345/156 |

OTHER PUBLICATIONS

E.G. Henneke and S.S. Russell, "Vibrothermography", *Nondestructive Testing Handbook, Special Nondestructive Testing Methods,* vol. 9, Am.Soc.NDT, pp. 336–340, 1995.

R.B. Mignona, R.E. Green, J.C. Duke, E.G. Henneke and K.L. Reifsnider, "Thermographic Investigation of High Power Ultrasonic Heating in Materials", Ultrasonics, pp. 159–163, Jul. 1981.

"Lockin–Thermographie", Institut for Kunststoffprufung und Kunststoffkunde/Abteilung Zerstorungsfreie Prufung, Pfaffenwaldring 32 70 569 Stuttgart.

J. Rantala et al., "Lock–in Thermography with mechanical loss angle heating at ultrasonic frequenices", QIRT 96—Eurotherm Series 50—Edizioni ETS, Pisa 1997, pps. 389–393.

Zhang, Daqing and Sandor, Bela I., ASTM Special Technical Publication, 10th Conf. on Composite Materials: Testing and Design, 1992 ASTM, pp. 428–443.

* cited by examiner

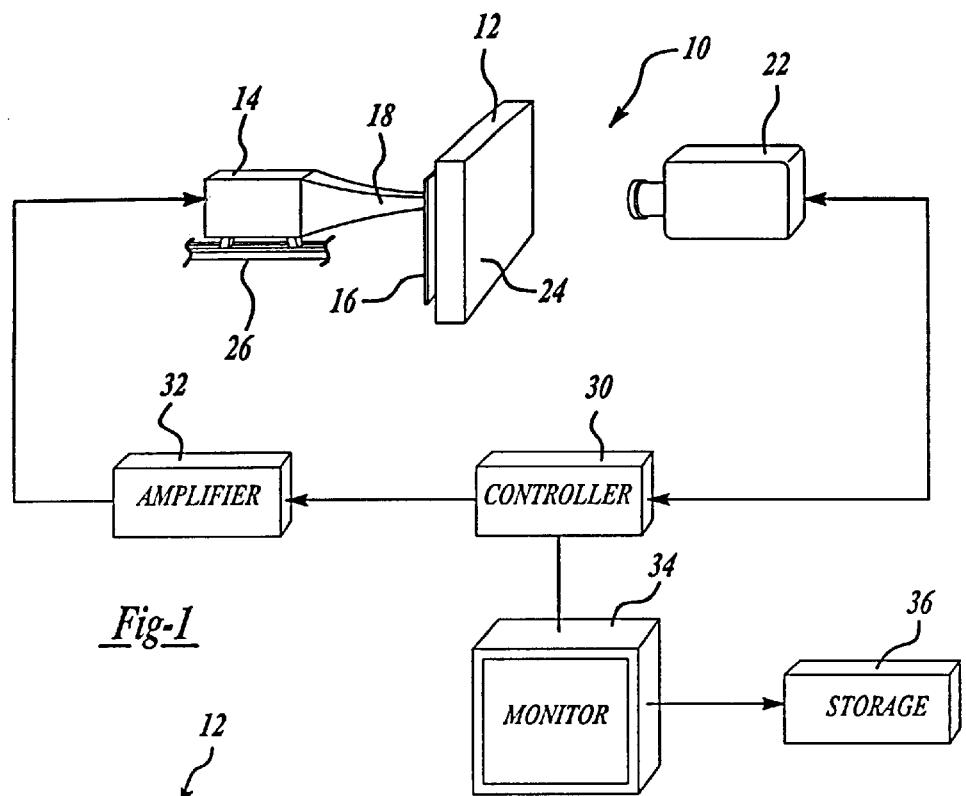
Fig-1
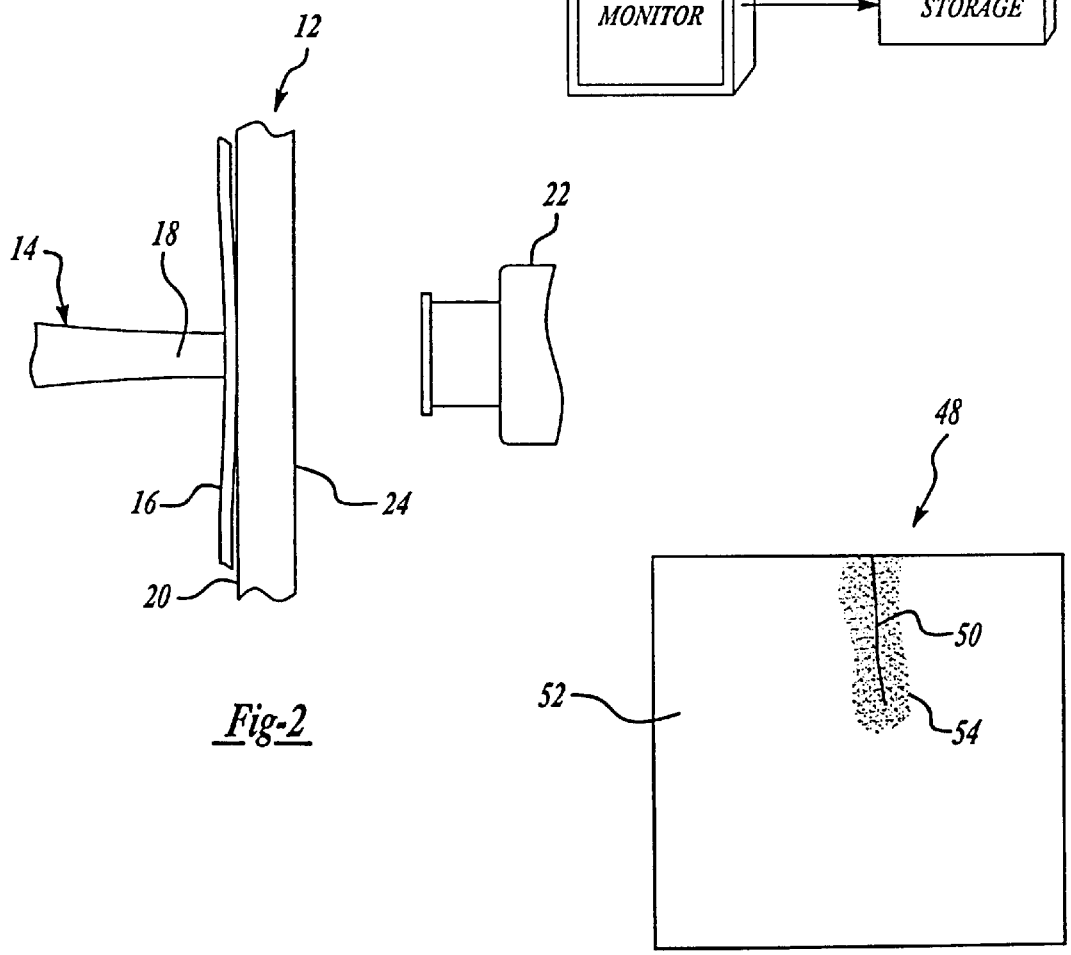
Fig-2
Fig-6

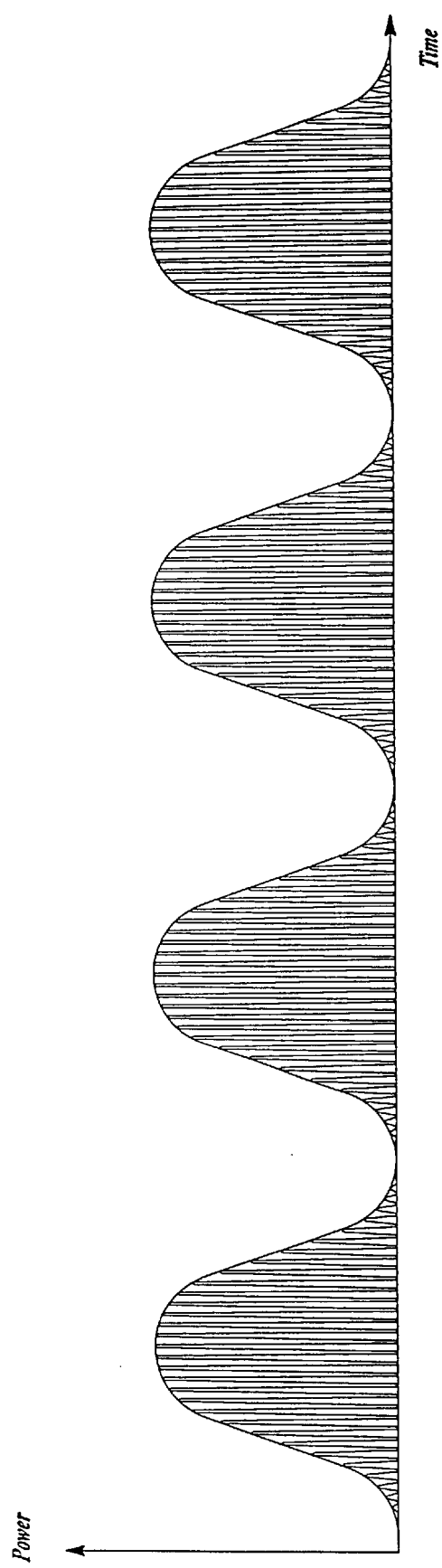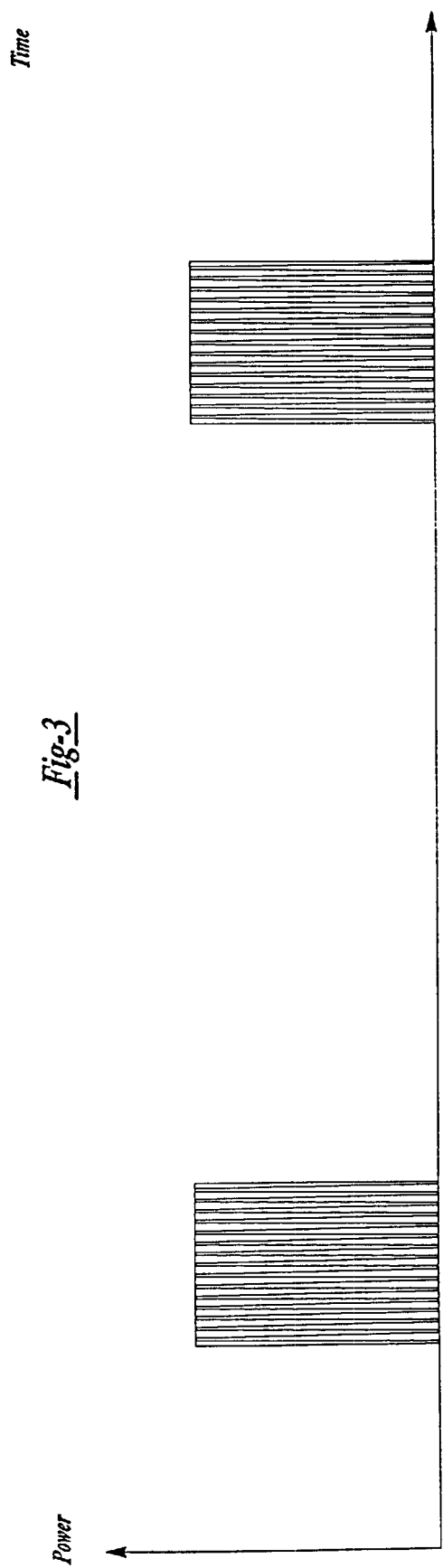

HAND-HELD SOUND SOURCE GUN FOR INFRARED IMAGING OF SUB-SURFACE DEFECTS IN MATERIALS

CROSS-REFERENCE TO RELATED APPLICATION

This application is a continuation-in-part application of U.S. patent application Ser. No. 09/397,585, titled Infrared Imaging of Ultrasonically Excited Subsurface Defects in Materials, filed Sep. 16, 1999 now U.S. Pat. No. 6,236,049 issued May 22, 2001.

BACKGROUND OF THE INVENTION

1. Field of the Invention

This invention relates generally to a system for detecting defects in a structural component by exciting the component with sound energy and then infrared imaging the component and, more particularly, to a hand-held sound source gun that includes stabilizing legs, and is applicable to be used in a system for detecting defects in materials.

2. Discussion of the Related Art

Maintaining the structural integrity of certain components and structures is very important in many areas because of safety concerns and the like. Loss of structural integrity is typically caused by material defects, such as cracks, delaminations, disbonds, corrosion, inclusions, voids and the like, that may exist in the component or structure. For example, it is very important in the aviation industry that reliable techniques are available to examine the structural integrity of the aircraft skin and structural components of the aircraft to ensure that the aircraft does not suffer from structural failure when in flight. The structural integrity of turbine blades and rotors, and vehicle cylinder heads is also important in those industries. Therefore, techniques have been developed for the non-invasive and non-destructive analysis of different structural components and materials in various industries.

One known technique for non-invasive and non-destructive testing for material defects includes treating the structural component with a dye penetrant so that the dye enters any crack or defects that may be present in the material. The component is then cleaned, and the structure is treated with a powder that causes the dye remaining in the cracks to wick into the powder. An ultraviolet (UV) light source is used to inspect the material to observe locations on the component that fluoresces as a result of the dye. This technique has the disadvantage, however, that it is highly inspector intensive and dependent because the person inspecting for the fluorescence must be skilled. Additionally, the dye does not typically penetrate tightly closed cracks or cracks that are not on the surface.

A second known technique for inspecting a component for defects employs an electromagnetic coil to induce eddy currents in the component. The coil is moved around on the component, and the eddy current pattern changes at a crack or other defect. The complex impedance in the coil changes as the eddy current changes, which can be observed on an oscilloscope. This technique has the drawback that it is also very operator intensive, and also extremely slow and tedious.

Another known technique employs thermal imaging of the component to identify the defects. Typically, a heat source, such as a flash lamp or a heat gun, is used to direct a planar pulse of heat to the surface of the component. The material of the component absorbs the heat, and emits reflections in the infrared wavelengths. Certain types of defects will cause the surface temperature to cool at a different rate over the defects than for the surrounding areas. A thermal or infrared imaging camera is used to image the component and detect the resulting surface temperature variation. Although this technique has been successful for detecting disbonds and corrosion, it is ordinarily not successful for detecting vertical cracks in the material, that is, those cracks that are perpendicular to the surface. This is because a fatigue crack looks like a knife edge to the planar heat pulse, and therefore no, or minimal, reflections occur from the crack making the cracks hard or impossible to see in the thermal image.

Thermal imaging for detecting defects in a material has been extended to systems that employ ultrasonic excitation of the material to generate the heat. The article Rantala, J. et al, "Lock-in Thermography with Mechanical Loss Angle Heating at Ultrasonic Frequencies," Quantitative Infrared Thermography, Eurotherm Series 50, Edizioni ETS, Pisa 1997, pg 389–393 discloses such a technique. In this technique, ultrasonic excitation is used to cause the crack or defect to "light up" as a result of the ultrasonic field. Particularly, the ultrasonic waves cause the opposing edges of the crack to rub together causing the crack area to heat up. Because the undamaged part of the component is only minimally heated by the ultrasonic waves, the resulting thermal images of the material show the cracks as bright areas against a dark background field.

The transducer used in the ultrasonic thermal imaging technique referred to above makes a mechanical contact with the component being analyzed. However, it is difficult to couple high power ultrasonic energy into some materials, particularly in the case of metals. Significant improvements in this technique can be achieved by improving the coupling between the ultrasonic transducer and the component.

Additionally, the known ultrasonic thermal imaging technique employs complex signal processing, particularly vector lock-in, synchronous imaging. Vector lock-in imaging uses a periodically modulated ultrasonic source and includes a processing technique that synchronously averages successive image frames producing an in-phase image and a quadrature image both based on the periodicity of the source. This results in images that are synchronous with the periodicity and eliminates unsynchronous noise from the image. The periodicity of the image can also be induced by an external stimulus, such as a modulated laser beam, heat lamps, etc. The processor receives the frames of video images and stores them synchronously with the induced periodicity, and then averages the stored frames with subsequently received frames to remove the noise. U.S. Pat. No. 4,878,116 issued Oct. 31, 1989 issued to Thomas et al discloses this type of vector lock-in imaging.

U.S. Pat. No. 5,287,183 issued to Thomas et al Feb. 15, 1994 discloses a synchronous imaging technique that is a modification of the vector lock-in imaging disclosed in the '116 patent. Particularly, the imaging technique disclosed in the '183 patent extends the vector lock-in synchronous imaging technique to include a "box car" technique variation where the source is pulsed, and the images are synchronously averaged at various delay times following each pulse. The box car technique multiplies the video signal by zero except in several narrow time windows, referred to as gates, which are at a fixed time delay from the initiation of each ultrasonic pulse. The effect of these gates is to acquire several images corresponding to the states of component being imaged at the predetermined fixed delay times after the pulses. These different delay times are analogous to the different phases, represented by the sine and cosine functions of the periodic signal in the lock-in technique. During the acquisition of the gated images, the images corresponding to different delay times are combined arithmetically by pixel-by-pixel subtraction to suppress non-synchronous background effects.

The ultrasonic excitation thermal imaging technique has been successful for detecting cracks. However, this technique can be improved upon to detect smaller cracks, as well as tightly closed cracks, with much greater sensitivity. It is therefore an object of the present invention to provide a defect detection system that uses sound energy to detect subsurface defects in materials, and particularly such a system that employs a hand-held sound source.

SUMMARY OF THE INVENTION

In accordance with the teachings of the present invention, a system is disclosed for infrared or thermal imaging of ultrasonically or sonically excited subsurface defects in a structure. The system includes a hand-held sound source, a thermal imaging camera and a control unit. The sound source emits pulses of sound energy into the structure, and the camera generates images of defects in the structure that are heated by the sound energy. The control unit controls the operation of the sound source and the camera for timing purposes.

The hand-held sound source provides a way of conveniently exciting many locations on a large structure, such as an aircraft fuselage. The sound source includes a transducer that is positioned against the structure at a desirable location. To prevent the transducer from "walking" on the structure when the pulses of sound energy are emitted, the source includes a pair of legs that are also positioned against the structure to define a plane in combination with the transducer. The length of each leg is adjustable relative to the length of the transducer so that the gun can be used against irregular surfaces. The legs include a rubber tip to further prevent the transducer from slipping on the structure. In an alternate embodiment, the gun includes three transducers that define a plane and act to stabilize the gun against the structure.

Additional objects, advantages and features of the present invention will become apparent from the following description and the appended claims when taken in conjunction with the accompanying drawings.

BRIEF DESCRIPTION OF THE DRAWINGS

FIG. 1 is a block diagram of an imaging system according to the invention;

FIG. 2 is a broken-away, side view of the transducer, specimen and camera of the imaging system shown in FIG. 1;

FIG. 3 is a graph with power on the vertical axis and time on the horizontal axis showing the ultrasonic signal used in the known thermal imaging techniques that employ vector lock-in synchronous imaging;

FIG. 4 is a graph with power on the vertical axis and time on the horizontal axis showing the pulsed ultrasonic signal used in the thermal imaging technique of the present invention;

FIG. 6 is an image generated by the imaging system of the invention, showing a closed crack excited by ultrasonic energy;

DETAILED DESCRIPTION OF THE PREFERRED EMBODIMENTS

Figure 5A:
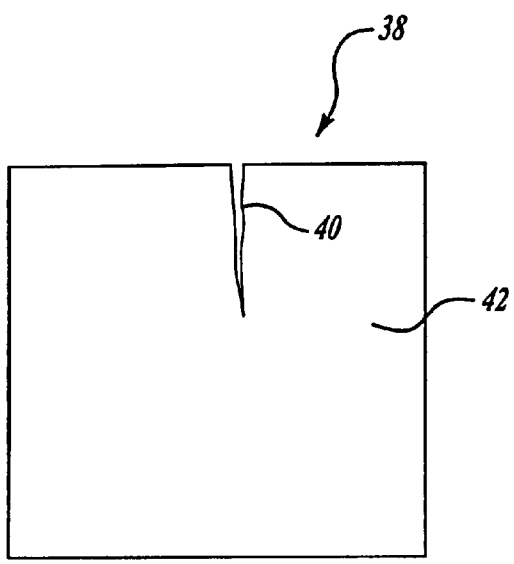
FIGS. 5(a)–5(d) show consecutive images at predetermined time intervals of an open crack in a specimen that has been ultrasonically excited and imaged by an imaging system of the present invention.

The following description of the preferred embodiments directed to an ultrasonic and thermal imaging system including a hand-held sound source gun is merely exemplary in nature, and is in no way intended to limit the invention or its applications or uses.

FIG. 1 is a block diagram of an imaging system 10, according to an embodiment of the present invention. The imaging system 10 is being used to detect defects, such as cracks, corrosion, delaminations, disbonds, etc., in a specimen 12. The specimen 12 is intended to represent any structural component or material, such as an aircraft skin, that may include these types of defects. It is stressed that the specimen 12 does not need to be metal, but can be other materials, such as ceramics, composites, etc. The system 10 includes an ultrasonic transducer 14 having a piezoelectric element that generates sonic or ultrasonic energy within a certain frequency band. The transducer 14 can be any transducer suitable for the purposes described herein, such as the Branson 900 MA ultrasonic transducer. In one embodiment, the ultrasonic transducer 14 generates a pulse of ultrasonic energy having a substantially constant amplitude at a frequency of about 20 kHz for a period of time of about ½ of a second and at a power level of about 1 kW. However, as will be appreciated by those skilled in the art, other ultrasonic frequencies, power levels and pulse durations can be used within the scope of the present invention.

The ultrasonic energy from the transducer 14 is coupled to the specimen 12 through a coupler 16. The coupler 16 is in mechanical contact with an end 18 of the transducer 14 and a front side 20 of the specimen 12. FIG. 2 is a broken-away, side view showing the transducer 14 in contact with the coupler 16 and the specimen 12. A support structure 26 is used to help maintain the transducer 14 in contact with the coupler 16. In one embodiment, the coupler 16 is a thin piece of a soft metal, such as copper, to effectively couple the ultrasonic energy into the specimen 12. Of course, other couplers consistent with the discussion herein can be used. For example, the coupler 16 can be a piece of cardboard or automotive gasket material. The coupler 16 can be any suitable piece of material that is typically softer than the end 18 of the transducer 14, and is malleable to be deformed against the end 18 of the transducer 14 and prevent the transducer 14 from bouncing or walking along the specimen 12. In one embodiment, the coupler 16 couples about 30 to 40 percent of the ultrasonic energy from the transducer 14 into the specimen 12. It is noted, however, that the coupler 16 may not be needed in certain applications, such as testing for defects in a composite.

A thermal imaging camera 22 is provided and spaced from a back side 24 of the specimen 12, and generates images of the side 24 of the specimen 12 in association with ultrasonic excitations of the specimen 12. The camera 22 can be spaced from the specimen 12 any suitable distance to provide images of as much of the specimen as desired in a single image. In other embodiments, the ultrasonic energy from transducer 14 and the image generated by the camera 22 can be provided at the same side of the specimen 12. The thermal camera 22 can be any camera suitable for the purposes described herein, such as the Galileo camera available from Raytheon. In one embodiment, the camera 22 senses infrared emissions in the 3–5 micron wavelength range, and generates images at 100 frames per second. The camera 22 includes a focal plane array having 256×256 InSb pixels to generate the resolution desirable. In one embodiment, the side 24 of the specimen 12 is painted black to provide better contrast for infrared imaging.

A controller 30 provides timing between the transducer 14 and the camera 22. The controller 30 can be any computer suitable for the purposes described herein. When the detection process is initiated, the controller 30 causes the camera 22 to begin taking sequential images of the specimen 12 at a predetermined rate. Once the sequence of images begins, the controller 30 sends a signal to an amplifier 32 that causes the amplifier 32 to send a pulse to the transducer 14 to generate the pulsed ultrasonic signal. The ultrasonic energy is in the form of a simple pulse at the frequency being used. It is not necessary to employ any type of vector lock-in or synchronous imaging techniques between the pulse of energy and the imaging, as is currently done in the prior art. However, such signal processing techniques can be used to further reduce noise. It is stressed that the frequencies and pulse time periods being described herein are by way of non-limiting examples, in that different ultrasonic frequencies, pulse times, input power, etc. will vary from system to system and specimen being tested. After the end of the pulse, the controller 30 instructs the camera 22 to stop taking images. The images generated by the camera 22 are sent to a monitor 34 that displays the images of the side 24 of the specimen 12. The images can then be sent to a storage device 36 to be viewed at another location if desirable.

The ultrasonic energy applied to the specimen 12 causes faces of the defects and cracks in the specimen 12 to rub against each other and create heat. This heat appears as bright spots in the images generated by the camera 22. Therefore, the system is very good at identifying very small tightly closed cracks. For those cracks that may be open, where the faces of the crack do not touch, the heating is generated at the stress concentration point at the crack tip. This point appears as a bright spot on the images indicating the end or tip of an open crack. The ultrasonic energy is effective to heat the crack or defect in the specimen 12 no matter what the orientation of the crack is relative to the energy pulse. The camera 22 takes an image of the surface 24 of the specimen 12, providing a visual indication of any crack in the specimen 12 no matter what the position of the crack within the thickness of the specimen 12.

The present invention provides improvements over the known ultrasonic and thermal imaging techniques because the ultrasonic pulses used to heat the cracks and defects are simple pulses having a substantially constant amplitude, and do not need to employ sinusoidal signal modulation as used in vector lock-in synchronous imaging. To illustrate this point, FIG. 3 shows a graph with power on the vertical axis and time on the horizontal axis depicting the waveform of the ultrasonic signal used in vector lock-in imaging. The ultrasonic signal is generated at a predetermined frequency, and modulated with a low frequency sinusoidal modulating wave that provides amplitude modulation at a predetermined modulation period. The ultrasonic frequency signal rises and falls in amplitude with the low frequency modulation wave. Typically, the ultrasonic excitation is performed over several seconds. The image generated by this imaging technique is not the actual image of the particular component being imaged, but is a difference image generated by the subtraction process of the synchronous imaging. A more detailed discussion of this type of vector lock-in synchronous imaging to reduce noise in these types of systems is discussed in the '116 patent.

FIG. 4 is a graph with power on the vertical axis and time on the horizontal axis showing the pulses used to provide the ultrasonic excitation in the present invention. The ultrasonic frequency signal within each pulse has substantially the same amplitude, and is not modulated by a lower frequency sinusoidal waveform. The images generated by the camera 22 are real images, and not difference images of the type generated in the vector lock-in synchronous imaging technique. This provides a significant improvement in image quality and control simplicity. Although one pulse is ordinarily sufficient, more than one pulse can be employed, separated in time by a predetermined time period, for signal averaging purposes to reduce noise. The technique of "box car" integration can be used as discussed in the '183 patent. In this technique, a gate is used in each time window to identify an image for each pulse, where the gate is at a certain fixed time delay from the beginning of the pulse. During the acquisition of the gated images, the images corresponding to different delay times are combined arithmetically to suppress non-synchronous background effects.

Figure 5B:
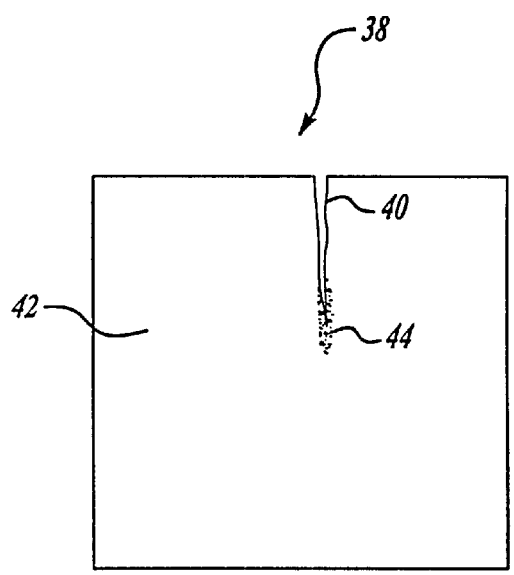
Figure 5C:
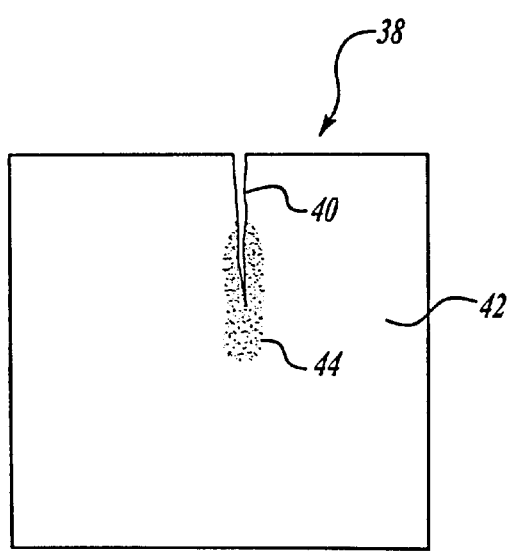
Figure 5D:
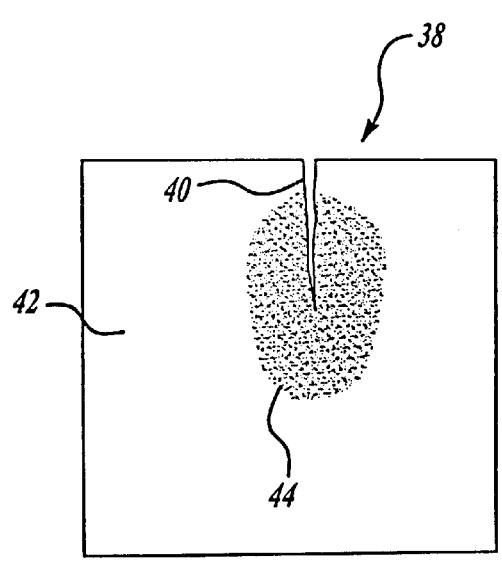

FIGS. 5(a)–5(d) show four sequential images 38 of an open fatigue crack 40 in a metal specimen 42. FIG. 5(a) shows the images 38 of the specimen 42 prior to the ultrasonic energy being applied. FIG. 5(b) shows the image 38 of the specimen 42 14 ms after the ultrasonic energy is applied. As is apparent, a light (higher temperature) spot 44 (sketched as a dark region) appears at the closed end of the crack 40, where the mechanical agitation causes the heating. FIGS. 5(c) and 5(d) show subsequent images 38 at time equal to 64 ms and time equal to 114 ms, respectively. The light spot 44 on the specimen 42 increases dramatically over this sequence, clearly indicating the location of the crack 40.

FIG. 6 shows an image 48 of a closed crack 50 in a specimen 52 after being energized by the ultrasonic pulse. In this embodiment, because the crack 50 is closed, the entire length of the crack 50 generates heat creating a light spot 54 along the entire length of the crack 50 and providing an indication of a closed crack. Because the ultrasonic energy is so effective in causing the closed crack 50 to heat up significantly relative to the background, very short closed cracks, for example on the order of ⅔ mm, are readily ascertainable in the image 48.

Figure 7:
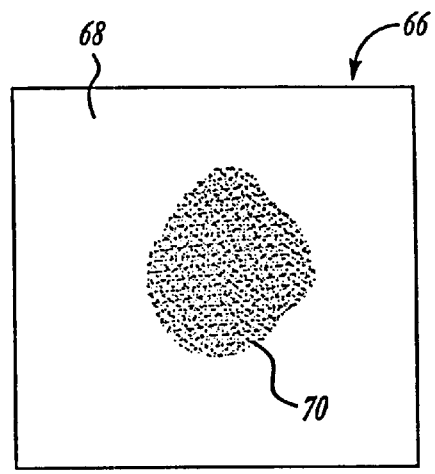
FIG. 7 is an image generated by the imaging system of the present invention, showing a delamination or disbond excited by the ultrasonic energy.

FIG. 7 shows an image 66 of a specimen 68. In this image, a light spot 70 is shown, and is intended to represent the type of image generated from the thermal energy that is created by ultrasonically exciting a delamination or disbond. The thermal imaging technique of the present invention is particularly useful in identifying "kissing" disbonds.

Figure 8:
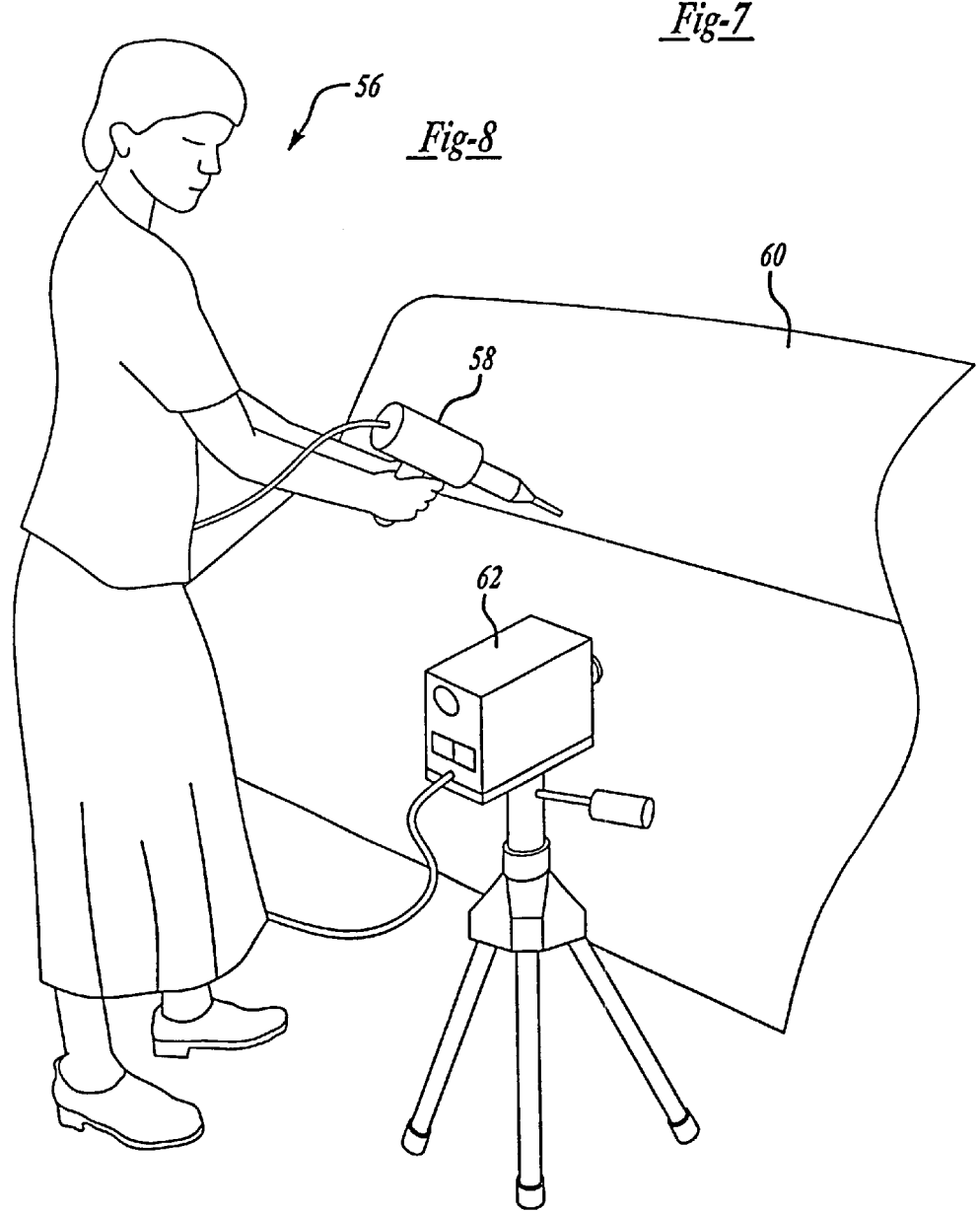
FIG. 8 is a perspective view of a person holding an ultrasonic transducer against an aircraft component, and using the imaging system of the present invention to detect cracks in the component.

FIG. 8 is a perspective view of an operator 56 holding a hand-held transducer 58 against a specimen 60, such as an aircraft fuselage. A thermal imaging camera 62 is directed towards the specimen 60 at a location that is separate from the point of contact of the transducer 58. FIG. 8 illustrates that the system according to the invention can be used in the field for testing such components.

For certain applications, the hand-held transducer 58 has limitations because it tends to "walk" or move on the structure when the pulse energy is emitted. Movement of the transducer 58 during the test reduces the coupling of the transducer 58 to the structure, thus reducing the amount of sound energy entering the structure and the quality of the resulting images. Thus, the ability to detect certain types of defects and possibly very small defects is limited.

Figure 9:
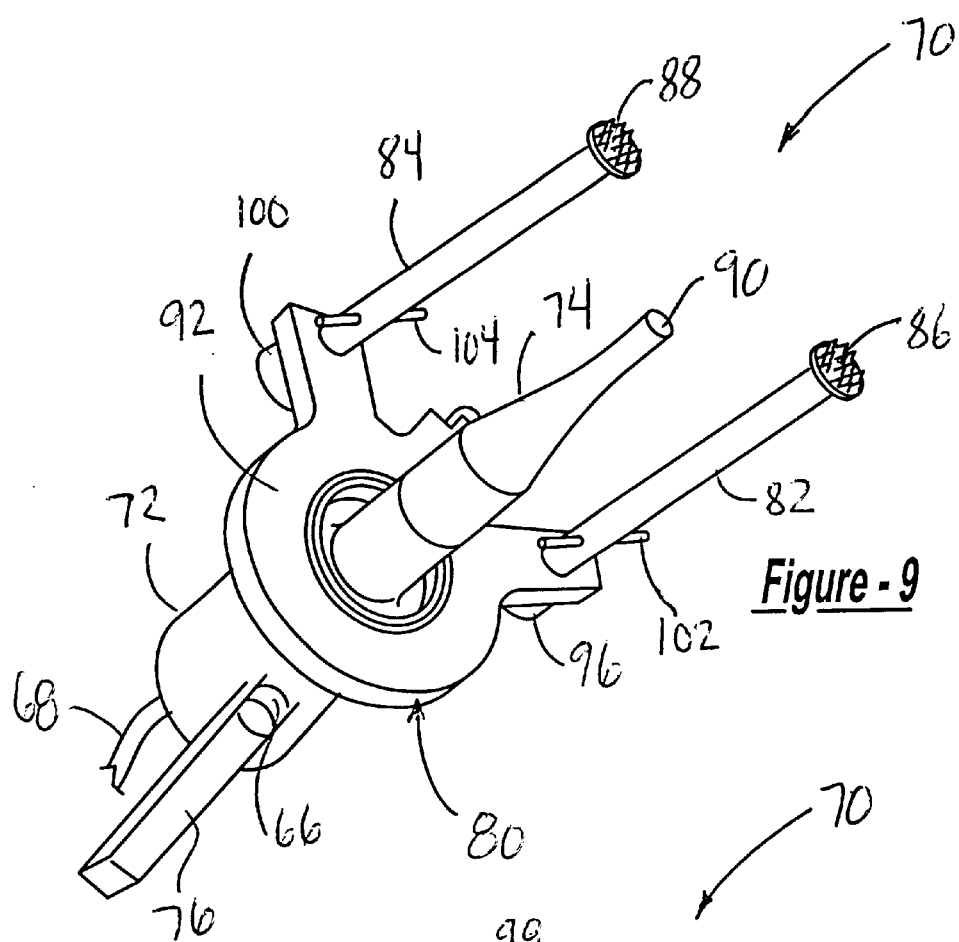
FIG. 9 is a perspective view of a hand-held, sound source gun for exciting a structure, according to an embodiment of the present invention.
Figure 10:
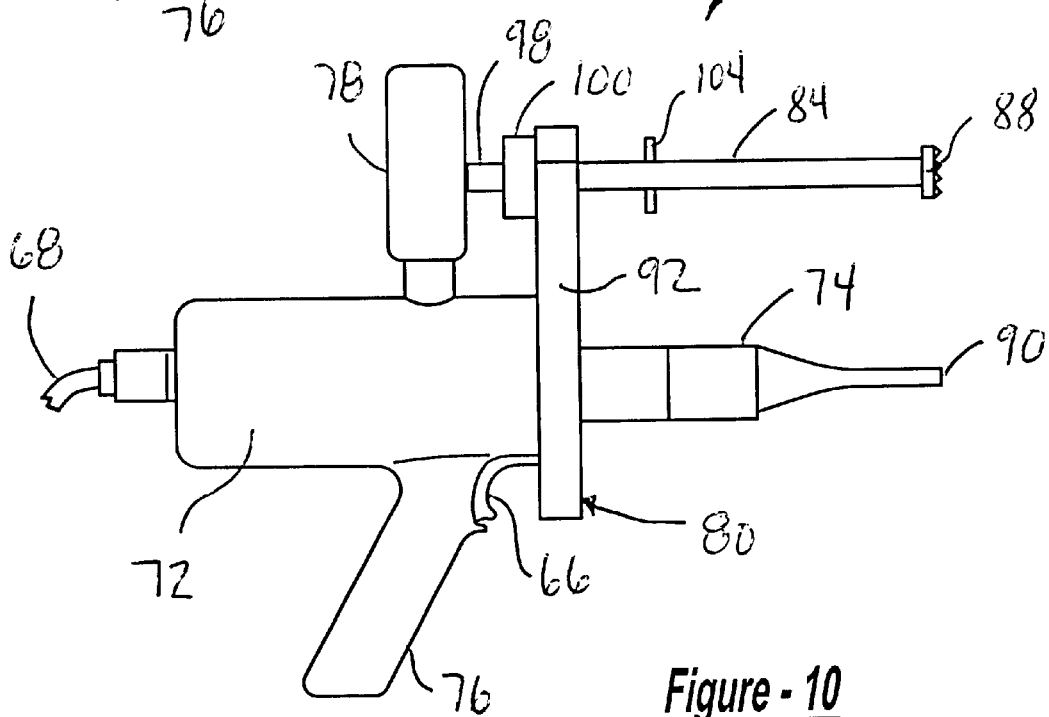
FIG. 10 is a side view of the gun shown in FIG. 9.
Figure 11:
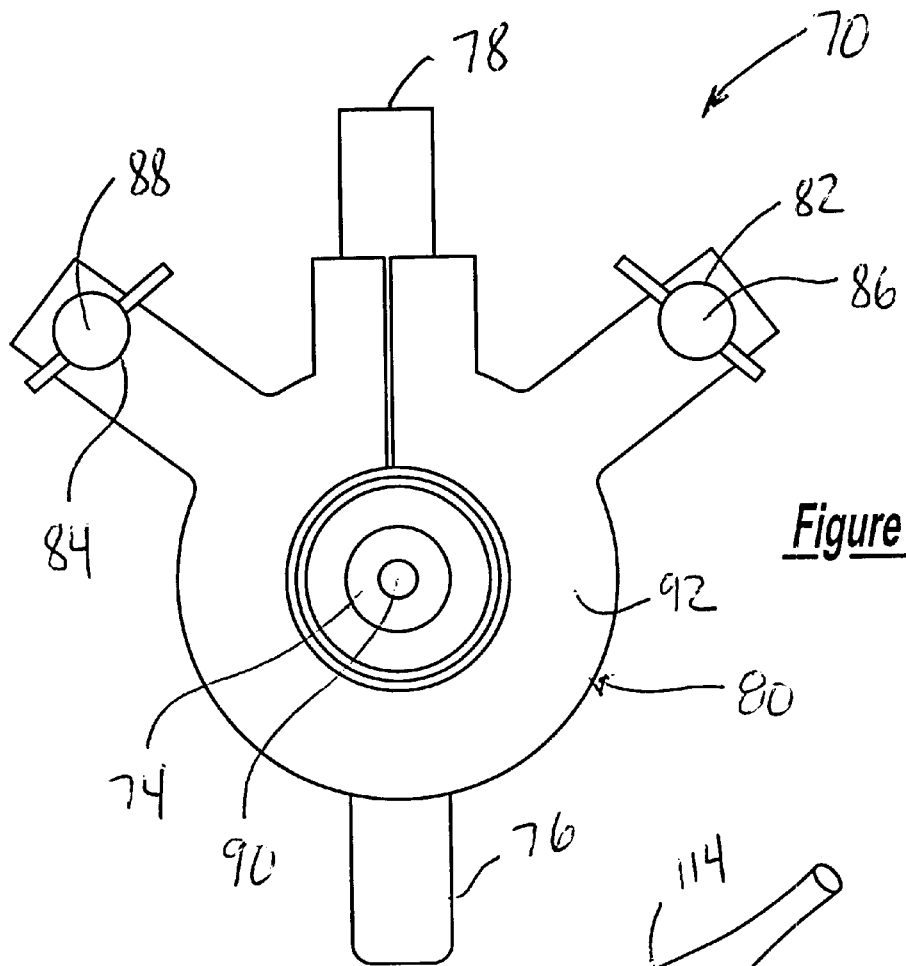
FIG. 11 is a front view of the gun shown in FIG. 9.

To overcome this limitation, the present invention proposes a modified hand-held, sound source gun 70 as depicted in FIGS. 9–11. The gun 70 includes a housing 72 that includes the components for generating the sound signal, as would be well understood to those skilled in the art. A transducer horn 74 is threadably mounted to one end of the housing 72 and extends therefrom. Thus, the horn 74 can be removed from the housing 72. One end of an electrical cable 68 is attached to the housing 72 at an end opposite from the horn 74, and an opposite end of the cable 68 is connected to the control unit, as discussed above. Further, a pistol-type grip 76 extends from a bottom of the housing 72, and a stabilizing grip 78 extends from a top of the housing 72 to allow an operator to firmly grip the gun 70 during testing. A trigger switch 66 on the grip 76 allows the operator to activate the sound source.

The gun 70 further includes a bracket assembly 80 clamped to an end of the housing 72 proximate the horn 74, as shown. The bracket assembly 80 can be clamped to the housing 72 in any suitable manner for the purposes described herein. The bracket assembly 80 includes a first leg 82 and a second leg 84 mounted thereto. The legs 82 and 84 are substantially parallel to the horn 74, and are about the same length. The bracket assembly 80 includes a base plate 92 that has a particular shape suitable to position the legs 82 and 84 a certain distance apart, as shown. The first leg 82 includes a rubber tip 86 and the second leg 84 includes a rubber tip 88 opposite the housing 72. The rubber tips 86 and 88 allow the gun 70 to be more firmly positioned against the structure to prevent slipping. The tips 86 and 88 can be made of other, non-slip materials, as would be appreciated by those skilled in the art. The operator places the tip 90 of the horn 74 and the tips 86 and 88 of the legs 82 and 84, respectively, against the structure being tested. The combination of the horn 74 and the legs 82 and 84 define a plane that prevents the horn 74 from moving when it is activated.

The first leg 82 also includes a tip 94 that is threadably attached to and extends through the bracket assembly 80 and is secured thereto by a lock nut 96. Likewise, the second leg 84 includes a tip 98 that is threadably attached to and extends through the bracket assembly 80 and is secured thereto by a lock nut 100. The leg 82 includes a pin 94 and the leg 84 includes a pin 96 that allow the legs 82 and 84 to be easily rotated. In this manner, the length of the legs 82 and 84 can be adjusted relative to the horn 74. This allows the gun 70 to be used against irregular surfaces.

Figure 12:
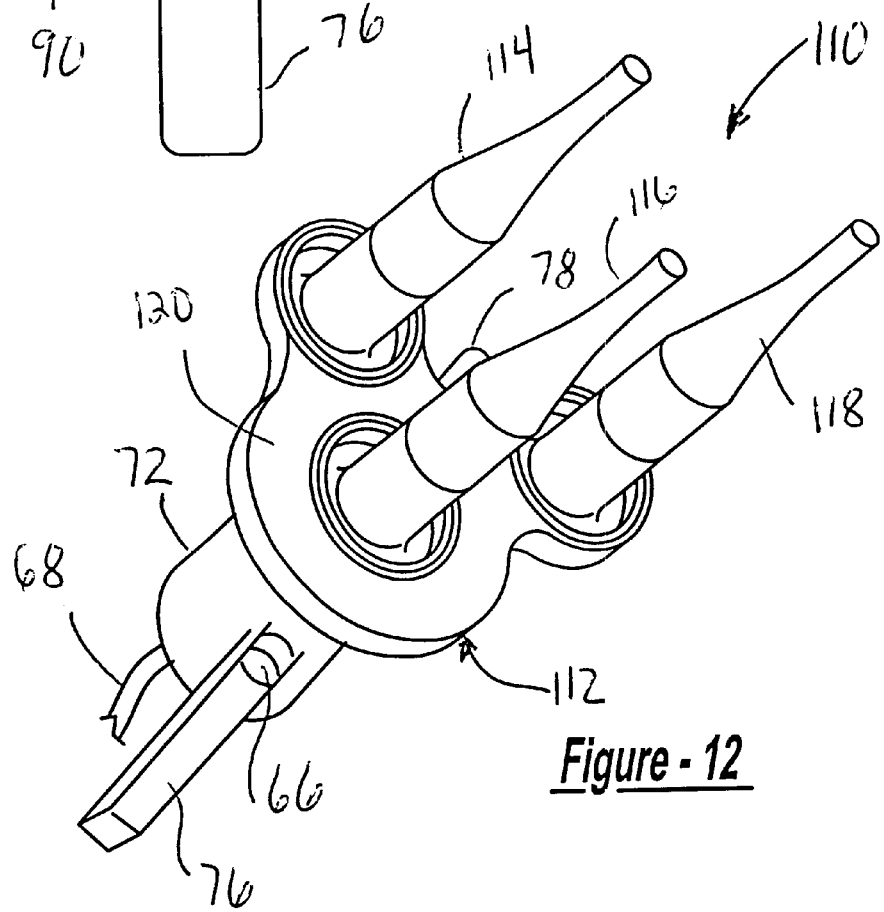
FIG. 12 is a perspective view of a hand-held, sound source gun for exciting a structure, according to another embodiment of the present invention.
Figure 13:
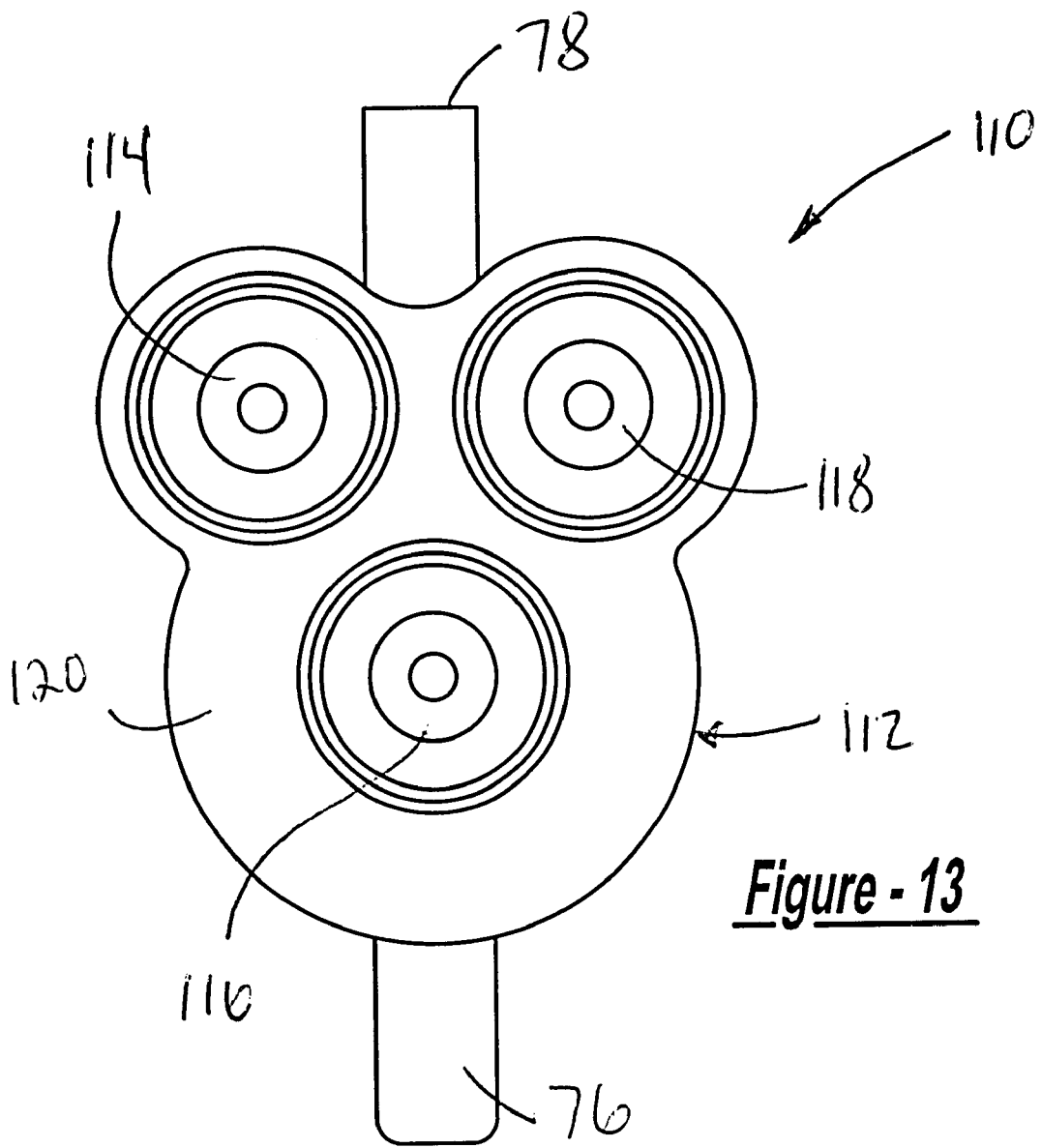
FIG. 13 is a front view of the gun shown in FIG. 12.

FIGS. 12 and 13 show a perspective view and a front view, respectively, of a hand-held gun 110 that is a modification of the gun 70, where like reference numerals identify the same components. As discussed above, the horn 74 is threaded into the housing 72 and can be removed therefrom. For the gun 110, the horn 74 and the bracket assembly 80 have been removed, and replaced with a horn structure 112. The structure 112 includes a threaded tip (not shown) that is threaded into the housing 72 in the same manner as the horn 74.

The structure 112 includes a base plate 120 and three horns 114, 116 and 118 symetrically disposed about the plate 120, as shown. The horns 114–118 are attached to the plate 120 by any suitable technique and can be integral therewith. The horns 114–118 provide the three leg foundation that defines a plane, and prevents the horns 114–118 from walking when the gun 110 is activated. The power from the sound generating components is distributed to the horns 114–118 evenly, which then enters the structure from three different locations.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A thermal imaging system for detecting defects in a component, said system comprising:
   a hand-held sound source gun, said gun including a housing, at least one handle coupled to the housing, at least one sound transducer coupled to the housing, and a stabilizing structure coupled to the housing, said stabilizing structure including two elongated members, wherein the combination of the at least one transducer and the two separate elongated members provide three separate stabilizing points operable to be positioned against the component to define a plane thereon;
   a thermal imaging camera directed towards the component and generating thermal images of the component; and
   a control unit electrically connected to the gun and the camera, said control unit causing the gun to emit pulses in a sound signal at a predetermined frequency and for a predetermined duration, and causing the camera to generate sequential images of the component, wherein the signal from the gun causes the defects in the component to heat up and be visible in the images generated by the camera.

2. The system according to claim 1 wherein the stabilizing structure includes a bracket mounted to the housing, and wherein the two elongated members are first and second cylindrical posts mounted to the bracket.

3. The system according to claim 2 wherein an end of the first and second posts opposite to the bracket includes a rubber member.

4. The system according to claim 1 wherein each of the two elongated members includes an adjusting device, the adjusting device being operable to adjust the length of the elongated member relative to the at least one transducer.

5. The system according to claim 1 wherein the at least one transducer is three transducers where two of the transducers are the two elongated members, and wherein the three transducers combined to deliver the sound signal to the component.

6. The system according to claim 5 wherein all three transducers are integral with the stabilizing structure.

7. The system according to claim 6 wherein the stabilizing structure is threadably mounted to the housing.

8. The system according to claim 1 wherein the at least one handle includes a first handle extending from a bottom of the housing and a second handle extending from a top of the housing.

9. The system according to claim 8 wherein the first handle is a pistol-type grip.

10. The system according to claim 1 wherein the frequency of the sound signal has a substantially constant amplitude.

11. The system according to claim 1 further comprising a coupler positioned between and in contact with the component and an end of the at least one transducer.

12. The system according to claim 11 wherein the coupler is malleable and is softer than the end of the transducer.

13. A defect detection system for detecting defects in a structure, said system comprising:
- a sound source gun, said gun including a housing, at least one sound transducer coupled to the housing, and a stabilizing device coupled to the housing, said stabilizing device including two separate elongated members, wherein the combination of the at least one transducer and the two separate elongated members provide three separate stabilizing points operable to be positioned against the structure, said gun delivering a sound signal to the structure to define a plane thereon;
- a camera directed towards the structure, said camera being responsive to radiation emitted from the structure and generating images of the structure when the gun emits the sound signal; and
- a control unit connected to the gun and the camera to provide timing signals therebetween, said control unit being responsive to the images from the camera.

14. The system according to claim 13 wherein the stabilizing device includes a bracket mounted to the housing, and wherein the two elongated members are first and second cylindrical posts mounted to the bracket.

15. The system according to claim 13 wherein an end of the first and second posts opposite to the bracket includes a rubber member.

16. The system according to claim 13 wherein each of the two elongated members includes an adjusting device, the adjusting device being operable to adjust the length of the elongated member relative to the at least one transducer.

17. The system according to claim 13 wherein the at least one transducer is three transducers where two of the transducers are the two elongated members, and wherein the three transducers combined to deliver the sound signal to the component.

18. The system according to claim 13 wherein all three transducers are integral with the stabilizing device.

19. The system according to claim 13 further including a first handle extending from a bottom of the housing and a second handle extending from a top of the housing.

20. A hand-held sound source gun for delivering sound energy to a structure, said gun comprising:
- a housing;
- at least one handle coupled to the housing;
- at least one sound transducer coupled to the housing; and
- a stabilizing device coupled to the housing, said stabilizing device including two separate elongated members, wherein the combination of the at least one transducer and the two separate elongated members provide three separate stabilizing points operable to be positioned against the structure to define a plane thereon.

21. The system according to claim 20 wherein the stabilizing device includes a bracket mounted to the housing, and wherein the two elongated members are first and second cylindrical posts mounted to the bracket.

22. The system according to claim 21 wherein an end of the first and second posts opposite to the bracket includes a rubber member.

23. The system according to claim 20 wherein each of the two elongated members includes an adjusting device, the adjusting device being operable to adjust the length of the elongated member relative to the at least one transducer.

24. The system according to claim 20 wherein the at least one transducer is three transducers where two of the transducers are the two elongated members.

25. The system according to claim 24 wherein all three transducers are integral with the stabilizing device.

26. The system according to claim 25 wherein the stabilizing device is threadably mounted to the housing.

27. The system according to claim 20 wherein the at least one handle includes a first handle extending from a bottom of the housing and a second handle extending from a top of the housing.

28. The system according to claim 27 wherein the first handle is a pistol-type grip.

29. A method of detecting defects in a structure, said method comprising the steps of:
- providing a hand-held sound source gun, said gun including a housing, at least one handle coupled to the housing, at least one transducer coupled to the housing, and a stabilizing device coupled to the housing, said stabilizing device including two separate elongated members, wherein the combination of the at least one transducer and the two separate elongated members provide three separate stabilizing points operable to be positioned against the component to define a plane thereon;
- emitting at least one pulse of a sound signal into the structure to heat the defects, said signal having a predetermined frequency; and
- generating a sequence of thermal images of the structure prior to, during and after the emission of the ultrasonic signal.

30. The method according to claim 29 wherein the step of providing a sound source gun includes providing two cylindrical posts mounted to a bracket attached to the housing, wherein the length of the posts relative to the length of the transducer is adjustable.

31. The method according to claim 29 wherein the step of providing a sound source gun includes providing three spaced apart transducers that make up the stabilizing device.

32. The method according to claim 31 wherein all of the three transducers are integral with the stabilizing device, and wherein the stabilizing device is threadably mounted to the housing.

33. The method according to claim 29 wherein the step of emitting at least one pulse of a sound signal includes emitting a sound signal pulse that has a substantially constant amplitude.

* * * * *

UNITED STATES PATENT AND TRADEMARK OFFICE
CERTIFICATE OF CORRECTION

PATENT NO. : 6,593,574 B2
DATED : July 15, 2003
INVENTOR(S) : Robert L. Thomas et al.

It is certified that error appears in the above-identified patent and that said Letters Patent is hereby corrected as shown below:

Column 9,
Line 15, insert -- to define a plane -- after "structure".
Line 16, delete "to define a plane" after "structure".

Signed and Sealed this

Twenty-seventh Day of September, 2005

JON W. DUDAS
*Director of the United States Patent and Trademark Office*